(12) United States Patent
McCreedy

(10) Patent No.: US 6,601,612 B2
(45) Date of Patent: Aug. 5, 2003

(54) DEVICE WITH PASSAGE FOR LIQUID

(75) Inventor: Thomas McCreedy, East Yorkshire (GB)

(73) Assignee: Micro Chemical Systems Limited, Hull (GB)

( * ) Notice: Subject to any disclaimer, the term of this patent is extended or adjusted under 35 U.S.C. 154(b) by 0 days.

(21) Appl. No.: 10/172,730

(22) Filed: Jun. 17, 2002

(65) Prior Publication Data

US 2003/0005968 A1 Jan. 9, 2003

(30) Foreign Application Priority Data

Jun. 18, 2001 (GB) ............................................ 0114840

(51) Int. Cl.$^7$ ................................................ F15C 1/04
(52) U.S. Cl. ........................ 137/827; 137/807; 137/833
(58) Field of Search ................. 137/827, 807, 137/833

(56) References Cited

U.S. PATENT DOCUMENTS

| | | | | |
|---|---|---|---|---|
| 4,173,299 A | * | 11/1979 | Kollberg et al. | ............ 137/827 |
| 4,908,112 A | * | 3/1990 | Pace | ........................ 210/198.2 |
| 5,658,413 A | * | 8/1997 | Kaltenbach et al. | ...... 156/272.8 |
| 5,681,751 A | * | 10/1997 | Begg et al. | .................... 436/89 |
| 6,167,910 B1 | * | 1/2001 | Chow | ........................ 137/827 |

FOREIGN PATENT DOCUMENTS

GB  2 351 245  12/2000

* cited by examiner

*Primary Examiner*—A. Michael Chambers
(74) *Attorney, Agent, or Firm*—Leydig, Voit & Mayer, Ltd.

(57) ABSTRACT

A microchip device has at least one passage along which a liquid can be moved by applying a voltage to the liquid. The device includes a passage member (10, 12) in which the passage is formed and which has an aperture (20, 22). Additionally the device includes an electrode member (14) that comprises an electrode (42, 44) and that is separably engageable with the passage member. The device includes a reservoir in fluid communication with the passages for holding a liquid. The electrode member cooperates with the aperture so that the electrode is in fluid communication with the passage without the electrode member obstructing the opening of the reservoir.

24 Claims, 2 Drawing Sheets

DEVICE WITH PASSAGE FOR LIQUID

The invention relates to a device including a passage along which a liquid may be moved by application of a voltage to the liquid.

The device may be suitable for performing a chemical reaction (including biochemical reactions), for performing a chemical separation (including biochemical separations) or for performing a chemical analysis (including biochemical analyses). Alternatively, the device may be used simply to move a liquid in a controlled manner, for example to introduce a predetermined quantity of liquid into another device where a chemical reaction, separation or analysis is to take place. Other uses of the device may be envisaged.

Throughout the specification, the term "liquid" will be used to include solutions and also liquids that carry non-dissolved material, for example suspensions.

A device of this type is described in GB 2351245. The device of GB 2351245 is formed from first and second members having respective surfaces. A plurality of grooves are provided in the surface of the first member. The surface of the second member is connected to the surface of the first member so that each groove is closed to form a respective passage. The passages interconnect. A plurality of openings extend through the second member and form liquid reservoirs in fluid communication with the passages. Liquids placed in the reservoirs can be moved through the passages, in a controlled manner, to perform chemical reactions. In order to move the liquids, voltages are applied to the liquids, by inserting electrodes into the reservoirs.

However, the insertion of electrodes into the reservoirs obstructs the reservoir openings and this can hinder the addition or removal of liquids to or from the reservoirs. Additionally, the insertion of the electrodes into the reservoirs distorts the hydrodynamics of the reservoirs.

According to a first aspect of the invention there is provided a device including a passage along which a liquid may be moved by application of a voltage to the liquid, comprising: a passage member in which the passage is formed and having an aperture; an electrode member comprising an electrode and being separably engageable with the passage member; and wherein, when the electrode member is in said engagement with the passage member, the device has a reservoir in fluid communication with the passage for holding a liquid, the reservoir having a base, the reservoir being continuous with the aperture, and the reservoir having an opening at a surface of the passage member, electrode member cooperating with the aperture so that the electrode is in fluid communication with the passage without the electrode occupying the opening and so that the electrode is located in the reservoir adjacent the base of the reservoir.

According to another aspect of the invention there is provided a device including a passage along which a liquid may be moved by application of a voltage to the liquid, comprising: a passage member which the passage is formed and having a aperture; an electrode member comprising an electrode and being separably engageable with the passage member; and wherein, when the electrode member is in said engagement with the passage member, the device has a reservoir in fluid communication with the passage for holding the liquid, the reservoir having an opening at a surface of the passage member, the electrode member cooperating with the aperture so that the electrode is in fluid communication with the passage without the electrode member occupying the opening, and wherein the electrode member cooperates with the passage member so that the aperture sealed to prevent liquid escape there from between the electrode member and the passage member.

According to another aspect of the invention there is provided a device including a passage along which a liquid may be moved by application of a voltage to the liquid, comprising: a passage member in which said passage is formed and having at least two apertures spaced from one another; an electrode member including at least two electrodes and a member that holds the electrodes in a spacing corresponding to the spacing of the apertures; the electrode member being separably engageable with the passage member, and wherein, when the passage member is in said engagement with the electrode member, each aperture is associated with a respective one of the electrodes so that electrode is in fluid communication with the passage.

The following is a more detailed description of embodiments of the invention, by way of example, reference being made to the appended schematic figures in which.

Figure 1:
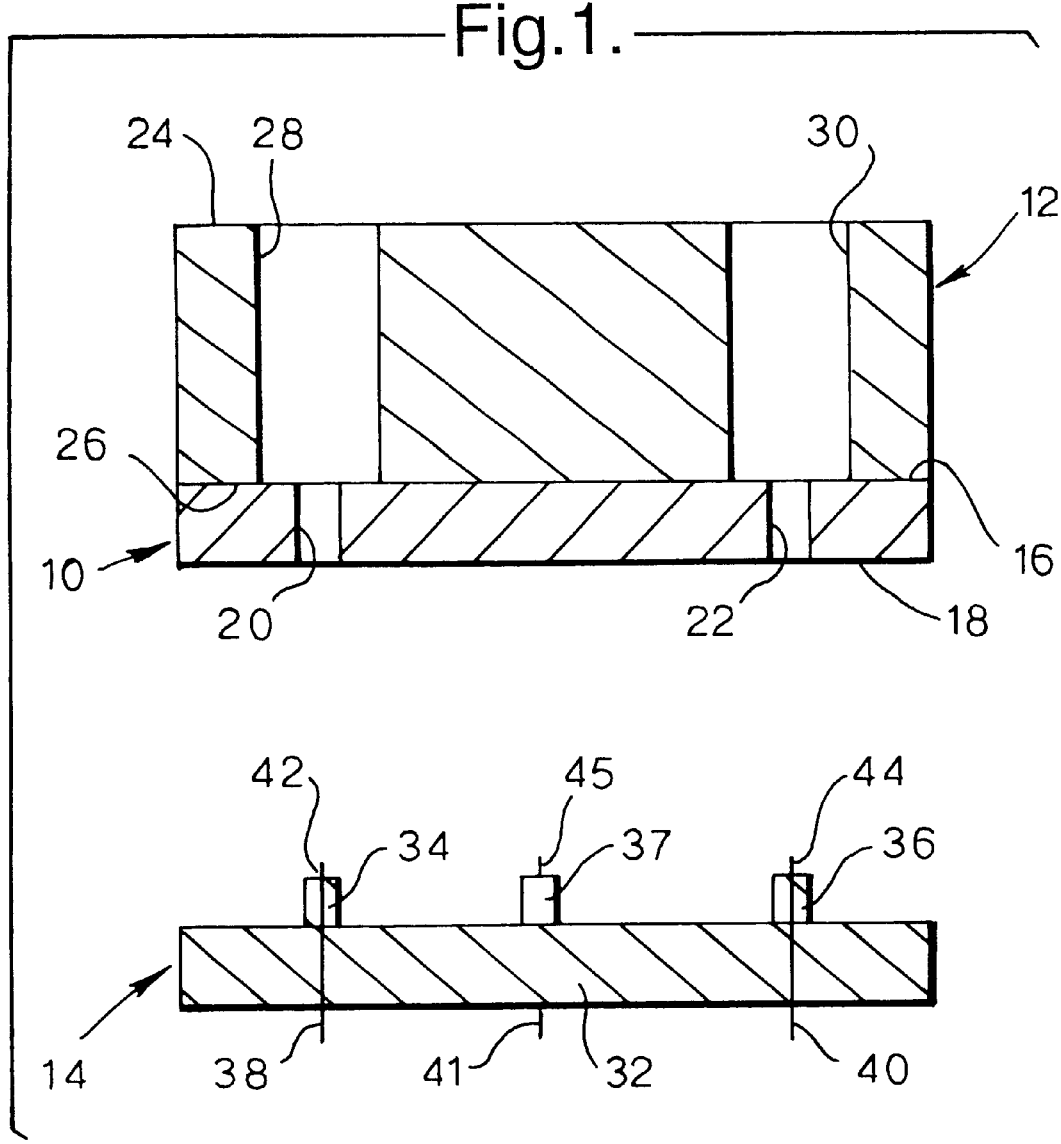
FIG. 1 is a schematic, cross-sectional view of a microchip device for conducting a chemical reation.

The microchip device consists of a first member 10, a second member 12 and an electrode member 14.

The first member 10 is formed from a block of borosilicate glass. The first member 10 has parallel, planar upper and lower surfaces 16, 18. First, second and third cylindrical apertures 20, 22, 19 extend between the upper and lower surfaces 16, 18 of the first member 10. The first and second apertures are shown at 20 and 22 in FIG. 1. The third aperture 19 (see FIG. 2) is identical and is located in a plane behind the plane of FIG. 1.

Figure 2:
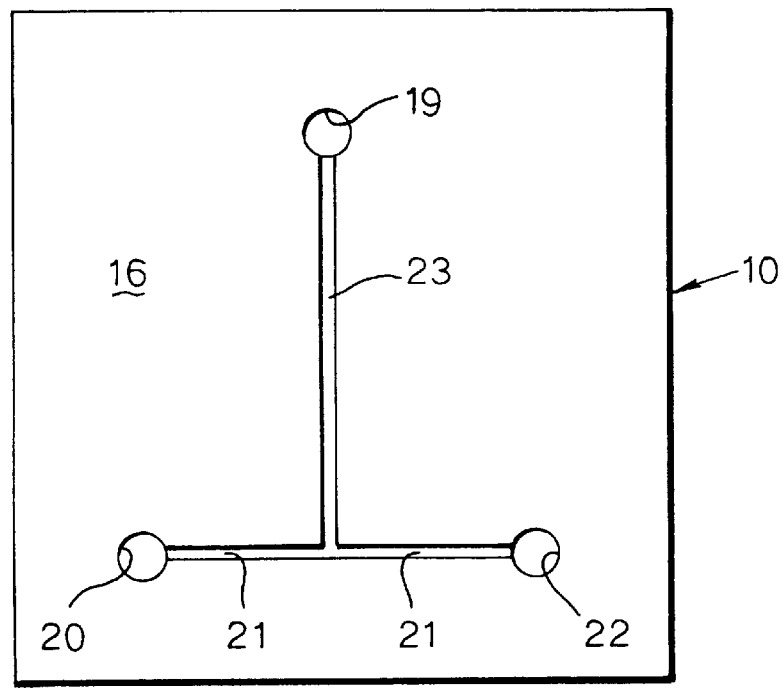
FIG. 2 is a plan view from above of a first member of the microchip device of FIG. 1.

As shown in FIG. 2, the upper surface 16 of the first member 10 is provided with a first groove 21 (not shown in FIG. 1 for clarity) which extends between the first and second apertures 20, 22. A second groove 23 is also formed in the upper surface 16 of the first member 10 and extends between the third aperture 19 and the mid-point of the first groove 21, connecting with the first groove 21. Hence the first and second grooves 21, 23 together form a T shape. Each of the first and second grooves 21, 23 has, for example, a width of approximately 300 micrometers and a depth of approximatly 115 micrometers (and are not shown to scale in FIG. 2). The grooves 21, 23 can be made in the upper surface 16 of the first member 10 by any known method, for example as described in GB 2351245.

Figure 3:
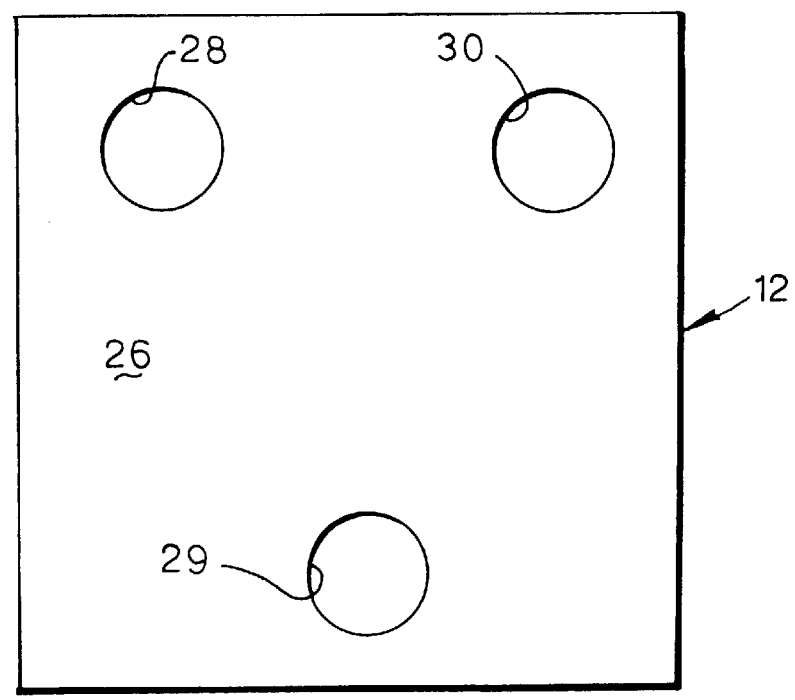
FIG. 3 is a plan view from below of a second member of the microchip device of FIG. 1.

The second member 12 is also formed from a block of borosilicate glass. The second member 12 has upper and lower planar, parallel surfaces 24, 26. First, second and third cylindrical holes 28, 30, 29 extend through the second member 12 between the upper and lower surfaces 24, 26. The first and second holes are shown in FIG. 1 at 28 and 30 respectively. The third hole (see FIG. 3) is located in a plane behind the plane of FIG. 1.

As can be seen in FIG. 1, the diameters of the first, second and third holes 28, 30, 29 in the second member 12 are greater than the diameters of the first, second and third cylindrical apertures 20, 22, 19 in the first member 10.

As indicated in FIG. 1, the lower surface 26 of the second member 12 is connected to the upper surface 16 of the first member 10 so that the first hole 28 lies above the first aperture 20, the second hole 30 lies above the second aperture 22, and the third hole 29 lies above the third aperture 19. Each hole, 28, 30, 29 shares a common axis with the corresponding aperture 20, 22, 19. The first and second members 10, 12 together will be referred to as the passage member.

The lower surface 26 of the second member 12 also closes the first and second grooves 21, 23 forming respective first and second interconnected passages in the form of a T. The first and second members 10, 12 can be connected together in any known manner, such as by standard thermal bonding or as described in GB 2351245.

The electrode member 14 comprises a support member 32 and first, second and third plugs 34, 36, 37 that are annular and that have outer cylindrical surfaces. The first and second plugs 34, 36 lie within the cross-sectional plane of FIG. 1. The third plug 37 lies behind the plane of FIG. 1.

A first conductor 38 extends through the support member 32, axially through the interior of the first plug 34 and has a portion that projects slightly from the upper end of the first plug 34 to form a first electrode 42. A second conductor 40 extends through the support member 32, axially through the interior of the second plug 36 and has a portion that projects from the upper end of the second plug 36 to form a second electrode 44. A third conductor 41 extends slimilarly through the support member 32, through the third plug 37 and has a portion that projects slightly beyond the upper end of the third plug 37 to form a third electrode 45. Each conductor 38, 40, 41 is sealed against the interior surface of the corresponding plug.

The spacing of the first, second and third plugs 34, 36, 37 corresponds to the spacing of the first, second and third cylindrical apertures 20, 22, 19 so that the first, second and third plugs 34, 36, 37 can be inserted, respectively, into the first, second and third cylindrical apertures 20, 22, 19 until the support member 32 contacts the lower surface 18 of the first member 10. The diameters of the plugs 34, 36, 37 and the apertures 20, 22, 19 are such that each plug 34, 36, 37 fits tightly within the corresponding aperture 20, 22, 19 so as to seal the apertures 20, 22, 19 and to prevent the passage of liquids between the plugs and the apertures.

As can be seen from the Figures, when the plugs 34, 36, 37 are inserted into the apertures 20, 22, 19 as described above, the first, second and third electrodes 42, 44, 45 lie just below and on the respective axes of the first, second and third holes 28, 30, 29. The upper ends of the three plugs 34, 36, 37 lie below the connected surfaces 16, 26. Hence, when the plugs 34, 36, 37 are engaged in the apertures 20, 22, 19 as described above, each hole 28, 30, 29, together with the portion of the corresponding aperture 20, 22, 19 located above the upper end of the corresponding plug 34, 36, 37 forms a reservoir for holding a liquid with the corresponding electrode 42, 44, 45 located at the base of the reservoir.

The electrode member 14 can be readily separated from the passage member simply by pulling the electrode member 14 away from the passage member whereupon the plugs 34, 36, 37 disengage from the apertures 20, 22, 19.

In use, the passage member is engaged with the electrode member 14 by engaging the plugs 34, 36, 37 into the corresponding apertures 20, 22, 19 as described above. The assembly is orientated with the upper surface 24 of the second member 12 horizontal and uppermost and the first, second and third conductors 38, 40, 41 are attached to a suitable voltage source.

Liquids suitable for performing a chemical reaction can then be added to the three reservoirs. Suitable electrical potentials are then applied to the first, second and third conductors 38, 40, 41 so as to cause the liquids to move through the passages, and to undergo a chemical reaction. The solutions move due to electro-osmotic and/or electrophoretic forces that are generated by the applied electrical potentials, as is well-known (see e.g. GB 2351245). As will be appreciated, the precise natures of the liquids and of the chemical reaction are not important to the current invention, and the skilled person will readily be able to determine chemical reactions suitable to be performed in this device.

A number of advantages are achieved using this microchip device. Firstly, the openings of the reservoirs (at the upper surface 24 of the second member 12) are nor obstructed by inserted electrodes. This facilitates addition and removal of liquids to and from the reservoirs. It also allows bubbles generated to escape freely. Secondly, the positioning of the electrodes at the bases of the reservoirs prevents or greatly reduces distortion of the hydrodynamics in the reservoirs. Thirdly, if the passage member (first member 10 and second member 12) needs replacing, either for cleaning or if it is damaged, it can be replaced by a similar passage member while retaining the same electrode member 14 (in which the conductors/electrodes can be made of expensive material).

The microchip device shown in the Figure may be altered.

For example, one or both of the passages may be filled with one or more porous structures, e.g. porous silica structures as described in GB 2351245.

Additionally, the number of passages may be altered. There may be any number of passages interconnected in any desired configuration. The number of the reservoirs can also be altered. Further, the number of electrodes may be changed, and may or may not be equal to the number of reservoirs.

Apertures can also be used to bring electrodes into fluid communication with a passage without the electrodes being in or close to a reservoir.

Some reservoirs may not need electrodes.

The passages can be of any suitable dimensions. Generally the passages will have no cross-sectional dimension greater than 500 $\mu$m.

The surfaces 16, 26 can be linked directly to one another or indirectly via an intermediate layer, for example, as described in GB 2351245.

The plugs 34, 36, 37 can be dispensed with. In this case the planar lower surface 18 of the first member 10 and the planar upper surface of the support member 32 are finely polished and form a fluid tight seal on contact. Other arrangements using O-rings or other resilient sealing members may be envisaged.

In the microchip described above, the electrode member cooperates with the apertures so that the electrodes are in fluid communication with the passages. This involves the conductors passing into the apertures. However, it is not necessary for the conductors to pass into the apertures. The electrodes could be on the surface of the support member 14 so that, for each aperture, the whole aperture forms part of a reservoir. The liquid in the apertures would then transmit the voltages to the passages.

I claim:

1. A device including a passage along which a liquid may be moved by application of a voltage to the liquid, comprising:

a passage member in which the passage is formed and having an aperture;

an electrode member comprising an electrode and being separably engageable with the passage member;

and wherein, when the electrode member is in said engagement with the passage member, the device has a reservoir in fluid communication with the passage for holding a liquid, the reservoir having an opening at a surface of the passage member, the electrode member cooperating with the aperture so that the electrode is in fluid communication with the passage without the electrode member occupying the opening, and wherein the electrode member cooperates with the passage member so that the aperture is sealed to prevent liquid escape therefrom between the electrode member and the passage member.

2. A device according to claim 1, wherein the electrode is associated with a plug formed on the electrode member, the plug fitting tightly within the aperture to seal the aperture.

3. A device according to claim 1, wherein the passage member and the electrode member have respective planar surfaces that contact one another to seal the aperture.

4. A device including a passage along which a liquid may be moved by application of a voltage to the liquid, comprising;

a passage member in which the passage is formed and having an aperture, an electrode member comprising an electrode and being separably engageable with the passage member;

and wherein, when the electrode member is in said engagement with the passage member, the device has a reservoir in fluid communication with the passage for holding a liquid, the reservoir having a base, the reservoir being continuous with the aperture, and the reservoir having an opening at a surface of the passage member, the electrode member cooperating with the aperture so that the electrode is in fluid communication with the passage without the electrode member occupying the opening, and so that the electrode is located in the reservoir adjacent the base of the reservoir.

5. A device according to claim 4, wherein the electrode member forms the base, sealing means being provided to prevent liquid leaking between the passage member and the electrode member.

6. A device according to claim 4, wherein the passage member is formed from first and second members having respective surfaces, a groove being provided in the first member surface, and the first and second members being connected together so as to close the groove and form said passage.

7. A device according to claim 6, wherein the aperture is formed in one of the first and second members and the reservoir is formed in the other one of the first and second members.

8. A device according to claim 7, wherein the aperture is cylindrical and the reservoir is cylindrical, the aperture sharing a common axis with the reservoir, the electrode lying on the axis.

9. A device according to claim 7, wherein the aperture is provided in the first member.

10. A device according to claim 4, wherein at least a part of the aperture forms at least part of the reservoir.

11. A device including a passage along which a liquid may be moved by application of a voltage to the liquid, comprising;

a passage member in which said passage is formed and having at least two apertures spaced from one another;

an electrode member including at least two electrodes and a member that holds the electrodes in a spacing corresponding to the spacing of the apertures;

the electrode member being separably engageable with the passage member, and wherein, when the passage member is in said engagement with the electrode member, each aperture is associated with a respective one of the electrodes so that each electrode is in fluid communication with the passage.

12. A device according to claim 11, wherein, when the passage member is in said engagement with the electrode member, the device includes at least two reservoirs in fluid communication with the passage.

13. A device according to claim 12, wherein each reservoir is continuous with a respective one of the apertures.

14. A device according to claim 13, wherein the passage member is formed from first and second members having respective surfaces, a groove being provided in the first member surface, and the first and second members being connected together so as to close the groove and form said passage.

15. A device according to claim 14, wherein the apertures are formed in one of the first and second members and the reservoirs are formed in the other one of the first and second members.

16. A device according to claim 15, wherein each aperture is cylindrical and each reservoir is cylindrical, each aperture sharing a common axis with the associated one of the reservoirs, each electrode lying on the corresponding one of the axes.

17. A device according to claim 15, wherein each aperture is provided in the first member.

18. A device according to claim 13, wherein at least a part of each aperture forms at least part of the associated reservoir.

19. A device according to claim 13, wherein each reservoir has a respective base, each electrode being located in a respective one of the reservoirs adjacent with the respective base.

20. A device according to claim 19, wherein the electrode member forms each base, sealing means being provided to prevent liquid leaking between the passage and electrode members.

21. A device according to claim 11, wherein the passage member is formed from first and second members having respective surfaces, a groove being provided in the first member surface, and the first and second members being connected together so as to close the groove and form said passage.

22. A device according to claim 11, wherein the electrode member cooperates with the passage member so that each aperture is sealed to prevent liquid escape therefrom between the electrode and passage members.

23. A device according to claim 22, wherein each electrode is associated with a respective plug formed on the electrode member, each plug fitting tightly within the associated one of the apertures to seal the aperture.

24. A device according to claim 22, wherein the passage member and the electrode member have respective planar surfaces that contact one another to seal each aperture.

* * * * *